(12) United States Patent
Buchanan et al.

(10) Patent No.: US 7,084,292 B2
(45) Date of Patent: Aug. 1, 2006

(54) INTEGRATED PROCESS FOR PREPARING DIALKYL CARBONATES WITH A CIRCULATING CATALYST

(75) Inventors: J. Scott Buchanan, Lambertville, NJ (US); Zhaozhong Jiang, Edison, NJ (US); Jose G. Santiesteban, Bethlehem, PA (US); William A. Weber, Burlington, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/887,642

(22) Filed: Jun. 22, 2001

(65) Prior Publication Data

US 2003/0045739 A1 Mar. 6, 2003

(51) Int. Cl.
 *C07C 69/96* (2006.01)

(52) U.S. Cl. .................................................. 558/277
(58) Field of Classification Search .................. 558/277
 See application file for complete search history.

(56) References Cited

U.S. PATENT DOCUMENTS

| | | | | |
|---|---|---|---|---|
| 2,773,070 | A | * 12/1956 | Lichtenwalter et al. | 549/230 |
| 2,873,282 | A | * 2/1959 | McClellan | 549/230 |
| 3,535,341 | A | 10/1970 | Frevel et al. | 260/340.2 |
| 3,642,858 | A | 2/1972 | Frevel et al. | 260/463 |
| 4,233,221 | A | * 11/1980 | Raines et al. | 549/230 |
| 4,434,105 | A | * 2/1984 | Buysch et al. | 260/463 |
| 4,691,041 | A | 9/1987 | Duranleau et al. | 558/277 |
| 5,218,135 | A | 6/1993 | Buysch et al. | |
| 5,489,703 | A | * 2/1996 | Pacheco et al. | 558/277 |
| 5,498,743 | A | 3/1996 | Shih et al. | |
| 5,498,744 | A | 3/1996 | Jentsch et al. | 558/277 |
| 6,010,976 | A | 1/2000 | Ryu | 502/156 |
| 6,207,850 | B1 | 3/2001 | Santiesteban et al. | |
| 6,342,623 | B1 | 1/2002 | Holgen et al. | |
| 6,407,279 | B1 | * 6/2002 | Buchanan et al. | 558/277 |
| 2003/0023109 | A1 | 1/2003 | Schlosberg et al. | 558/277 |

FOREIGN PATENT DOCUMENTS

| | | |
|---|---|---|
| DE | 4 326 906 | 2/1995 |
| EP | 0 119 840 | 9/1984 |
| EP | 0 460 732 | 12/1991 |
| EP | 0 478 073 | 4/1992 |
| EP | 0 534 545 | 3/1993 |
| EP | 1 125 915 | 8/2001 |
| GB | 2 107 712 | 5/1983 |
| WO | WO 00/73256 | 12/2000 |
| WO | WO 02/070452 | 9/2002 |
| WO | WO 03/000641 | 1/2003 |

OTHER PUBLICATIONS

John J. Mcketta et al., "Ethanol as Fuel: Options, Advantages, and Disadvantages to Exhaust Stacks, Cost," Encyclopedia of Chemical Processing and Design, vol. 20, pp. 237–243, year not available.
"Dimethyl Carbonate via Ethylene Carbonate," 90S7, Chem Systems, pp. 1–36 (Dec. 1991).
"Developments in Dimethyl Carbonate Production Technologies," 99/00S6, Chem Systems, pp. 1–73 (May 2000).
Shao–Hwa Wang, "The Coproduction of Dimethyl Carbonate and Ethylene Glycol by Transesterification," Process Economics Program, PEP Review No. 92–1–1, pp. 1–30 (May 1993).
J.J. McKetta et al., "Ethylene Carbonate and Propylene Carbonate," Encyclopedia of Chemical Processing and Design, pp. 177–201 (1984).
W.J. Peppel, "Preparation and Properties of the Alkylene Carbonates," Jefferson Chemical Co., vol. 50, No. 5, pp. 767–770 (May 1958).
Encyclopedia of Chemical Processing and Design, J.J. McKetta et al., "Ethylene Carbonate and Propylene Carbonate," New York, pp. 177–201, (1984).
DE 4 326 906 –Abstract of Patent (published Feb. 16, 1995).
Bhamage B.M., et al: "Synthesis of dimethyl carbonate and glycols from carbon dioxide, expoxides, and methanol using hetergenous basic metal oxide catalysts with high activity and selectivity", Applied Catalysis A: General, Elsevier Science, Amsterdam, NL, vol. 219, No. 1–2, pp. 259–266 (Oct. 5, 2001).
Hong Zhu et al: "Synthesis of Propylene Carbonate and Some Dialkyl Carbonates in the Presence of Bifunctional Catalyst Compositions", Polymers for Advanced Technologies, John Wiley & Sons, Chichester, GB, vol. 7, No. 8, pp. 701–703 (Aug. 1, 1996).
John J. McKetta et al., "Ethanol as Fuel: Options, Advantages, and Disadvantages to Exhaust Stacks, Cost," Encyclopedia of Chemical Processing and Design, New York, vol. 20, pp. 237–243, (1984).
Watanabe Y., et al: "Hydrotalcite–type Materials as Catalysts for the Synthesis of Dimethyl Carbonate from Ethylene Carbonate and Methanol", Microporous and Mesoporous Materials, Elsevier Science Publishing, New York, vol. 22, vol. 22, No. 1–3, pp. 399–407 (Jun. 17, 1998).

\* cited by examiner

*Primary Examiner*—Laura L. Stockton (57) ABSTRACT

An integrated process for the production of a dialkyl carbonate and a diol from an alkylene oxide, carbon dioxide and an aliphatic monohydric alcohol is described in which an alkylene oxide is first reacted with carbon dioxide in the presence of a homogeneous carbonation catalyst to provide a corresponding cyclic carbonate and the cyclic carbonate is then reacted with an aliphatic monohydric alcohol in the presence of the homogeneous carbonation catalyst and/or a heterogeneous transesterification catalyst and recycling the homogeneous carbonation catalyst to provide a corresponding dialkyl carbonate and diol.

16 Claims, 4 Drawing Sheets

INTEGRATED PROCESS FOR PREPARING DIALKYL CARBONATES WITH A CIRCULATING CATALYST

This invention relates to a process for preparing dialkyl carbonates and diols. More specifically the present invention relates to an integrated process for preparing dialkyl carbonates and diols from alkylene oxides, carbon dioxide and alcohols, using a circulating homogeneous carbonation catalyst and, optionally, a heterogeneous transesterification catalyst.

BACKGROUND OF THE INVENTION

Dialkyl carbonates are important intermediates for the synthesis of fine chemicals, pharmaceuticals and plastics and are useful as synthetic lubricants, solvents, plasticizers and monomers for organic glass and various polymers, including polycarbonate, a polymer known for its wide range of uses based upon its characteristics of transparency, shock resistance and processability.

One method for the production of polycarbonate resin employs phosgene and bisphenol-A as starting materials. However, this method has numerous drawbacks, including the production of corrosive by-products and safety concerns attributable to the use of the highly toxic phosgene. As such, polycarbonate manufacturers have developed non-phosgene methods for polycarbonate production, such as reacting diphenyl carbonate with bisphenol-A.

Dimethyl carbonate has a low toxicity and can also be used to replace toxic intermediates, such as phosgene and dimethyl sulfate, in many reactions, such as the preparation of urethanes and isocyanates, the quaternation of amines and the methylation of phenol or naphthols. Moreover, it is not corrosive and it will not produce environmentally damaging by-products. Dimethyl carbonate is also a valuable commercial product finding utility as an organic solvent, an additive for fuels, and in the production of other alkyl and aryl carbonates.

Dimethyl carbonate, as well as other dialkyl carbonates, have traditionally been produced by reacting alcohols with phosgene. These methods have the same problems as methods that use phosgene and bisphenol-A, i.e. the problems of handling phosgene and disposing of phosgene waste materials. Thus, there is a need for commercially viable non-phosgene methods for the production of dimethyl carbonate, as well as other dialkyl carbonates.

Non-phosgene methods that have been proposed for producing dialkyl carbonates include the transesterification reaction of alcohols and cyclic carbonates. Most of the proposed methods relate to the use of various catalysts for that reaction. Examples of such proposed catalysts include alkali metals or basic compounds containing alkali metals; tertiary aliphatic amines; thallium compounds; tin alkoxides; alkoxides of zinc, aluminum and titanium; a mixture of a Lewis acid and a nitrogen-containing organic base; phosphine compounds; quaternary phosphonium salts; cyclic amidines; compounds of zirconium, titanium and tin; a quaternary ammonium group-containing strongly basic anion-exchange solid material; a solid catalyst selected from the group consisting of a tertiary amine-or quaternary ammonium group-containing ion-exchange resin, a strongly acidic or a weakly acidic ion-exchange resin, a mixture of an alkali metal with silica, a silicate of an alkaline earth metal and an ammonium ion-exchanged zeolite; and a homogeneous carbonation catalyst selected from the group consisting of tertiary phosphine, tertiary arsine, tertiary stibine, a divalent sulfur compound and a selenium compound.

With respect to the method for carrying out the above-mentioned transesterification reaction between a cyclic carbonate and an alcohol, the proposed methods generally rely upon using commercial grade reactants (i.e., the cyclic carbonate and the alcohol) having a relatively high purity to achieve adequate reaction rate, yield and selectivity to the desired dialkyl carbonates and diols, as discussed more fully below.

It is known to react alkylene oxides with $CO_2$ in the presence of catalysts to give cyclic carbonates. The proposed methods for this reaction again mostly relate to the development of various catalysts. Examples of such proposed catalysts include alkali metal halides; ammonium, phosphonium or sulphonium halide carbonates; a combination of protic compounds, such as alcohols, and nitrogen-containing bases; arsonium halides; tertiary phosphines with alcohols; and alkali metal transfer catalysts with crown ethers and other ligands.

Although some of these proposed methods for producing cyclic carbonates will provide relatively high yields and selectivity to the desired cyclic carbonate, inevitably a significant amount of glycols are produced as by-products of the reaction between the alkylene oxides and $CO_2$. For example, the reaction between ethylene oxide and $CO_2$ to produce ethylene carbonate will inevitably produce a certain amount of ethylene glycol and higher molecular glycols, e.g., di- and tri-ethylene glycol. It is generally believed that the presence of these glycol impurities contained in the cyclic carbonate will adversely affect the transesterification reaction between the cyclic carbonate and an alcohol, since certain glycols, e.g., ethylene glycol, will typically unfavorably affect the equilibrium of the reaction, thereby lowering yield or possibly selectivity for the desired products. In addition, the glycols have hydroxyl (—OH) groups which would be expected to compete with the alcohol in reacting with the cyclic carbonate, forming unwanted heavier carbonates and other undesired species. Moreover, since the glycol impurities, e.g., ethylene glycol and triethylene glycol, are generally hygroscopic in nature, the cyclic carbonate containing these glycol impurities will tend to absorb water during storage. When water is present in sufficient quantity in the reaction mixture, hydrolysis takes place simultaneously with the transesterification reaction, resulting in a decrease in the selectivity for the dialkyl carbonate. Thus, in order to avoid the problems associated with the glycol impurities, the proposed methods for producing dialkyl carbonates from a cyclic carbonate have required a relatively high purity cyclic carbonate.

In order to provide a high purity commercial grade cyclic carbonate, e.g., ethylene carbonate, useful as a reactant in connection with the proposed methods discussed above, difficult separations have to be performed to achieve the requisite cyclic carbonate purity, resulting in increased operating and capital costs. Typically, the purification process for a cyclic carbonate, e.g., ethylene glycol, produced by reacting an alkylene oxide with $CO_2$, will include the following: (1) flashing the carbonation reactor effluent to remove the light ends; (2) passing the remaining liquid through one or more evaporators to remove and recycle catalyst, and to remove heavies; (3) distilling the crude product stream containing the cyclic carbonate and mono- and poly-glycols in a first vacuum distillation column, containing between about 8 and 50 trays, to remove the majority of the mono- and poly-glycols; and (4) distilling the purified cyclic carbonate stream in a finishing vacuum distillation column, containing between about 8 and 50 trays, to remove remaining polyglycols and other heavies and to provide a high purity cyclic carbonate.

There are significant capital and operating costs associated with the two vacuum distillation columns needed to provide a high purity cyclic carbonate. Moreover, a significant amount of the cyclic carbonate is generally lost as a result of the purification process. For example, in the case of ethylene carbonate, an azeotrope is formed in the first vacuum distillation column, which can contain about 91% ethylene glycol and 9% ethylene carbonate, depending upon the pressure in the column, so that a significant amount of ethylene carbonate is removed with the ethylene glycol. Further, depending upon the operating conditions of the distillation columns, and specifically the high temperatures associated with full reboiled columns, a certain amount of decomposition of the cyclic carbonate can occur resulting in additional losses. Moreover, additional cyclic carbonate is lost in connection with recycling the homogeneous carbonation catalyst and removing heavies from that catalyst recycle stream.

One patent that discloses a process for producing a dialkyl carbonate, which does not require a highly purified cyclic carbonate is U.S. Pat. No. 5,218,135 (Buysch et al.). The Buysch et al. patent discloses a process for the preparation of dialkyl carbonates from alkylene oxides, $CO_2$ and alkanols, where an alkylene carbonate is formed in a first step by reacting an alkylene oxide with $CO_2$ and then reacting the alkylene carbonate, formed in the first step, with an alkanol to form a dialkyl carbonate. It further discloses that the first step reaction is conducted in the presence of a bifunctional halide/lewis acid catalyst at pressures below 10 bar and the second reaction is conducted in the presence of the same bifunctional halide/lewis acid catalyst under autogenous pressure. However, there are problems associated with using this process on an industrial scale. The problems include long reaction times for the first step reaction between the alkylene oxide and $CO_2$, high corrosivity of many Lewis acids, thus making the process unattractive for use on an industrial scale.

As can be understood from the above, no proposal has heretofore been made with respect to the present invention's integrated process for producing a dialkyl carbonate and a diol from an alkylene oxide, carbon dioxide and an alcohol, having high productivity, which first reacts an alkylene oxide with carbon dioxide in the presence of a homogeneous carbonation catalyst to provide a cyclic carbonate and then feeds both the cyclic carbonate and the homogeneous carbonation catalyst to a second, transesterification reactor containing a heterogeneous transesterification catalyst. Additionally, no proposal has heretofore been made with respect to the present invention's integrated process useful on an industrial scale for producing a dialkyl carbonate and a diol from an alkylene oxide, carbon dioxide and an alcohol, having high productivity, which first reacts an alkylene oxide with carbon dioxide in the presence of a homogeneous carbonation catalyst to provide a cyclic carbonate and then feeds both the cyclic carbonate and the homogeneous carbonation catalyst to a second reaction zone to react the cyclic carbonate with an alcohol to provide a dialkyl carbonate and diol having relatively high conversion rates with high selectivity to the desired products.

SUMMARY OF THE INVENTION

According to the present invention, it has now been found that a dialkyl carbonate and a diol, and more specifically dimethyl carbonate and ethylene glycol, can be prepared according to an integrated process having high productivity which uses a homogeneous catalyst, by:

reacting an alkylene oxide (ethylene oxide in the case of dimethyl carbonate and ethylene glycol) with carbon dioxide in the presence of a homogeneous carbonation catalyst in a first reaction zone at a temperature in the range of about 50 to 250° C. and at a pressure of at least about 200 psi to provide a crude cyclic carbonate stream containing a cyclic carbonate (e.g., ethylene carbonate in the case of dimethyl carbonate and ethylene glycol) and homogeneous catalyst; and reacting the cyclic carbonate (e.g., ethylene carbonate) from the crude cyclic carbonate stream with an aliphatic monohydric alcohol (e.g., methanol in the case of dimethyl carbonate and ethylene glycol), in the second reaction zone in the presence of the homogeneous carbonation catalyst in the crude cyclic carbonate stream to provide a crude product stream containing a dialkyl carbonate (e.g. dimethyl carbonate) and diol (e.g. ethylene glycol).

In another aspect of the present invention, it has now been found that a dialkyl carbonate and a diol, and more specifically dimethyl carbonate and ethylene glycol, can be prepared according to an integrated process having high productivity by using both a homogeneous carbonation and heterogeneous transesterification catalyst, by:

reacting an alkylene oxide (ethylene oxide in the case of dimethyl carbonate and ethylene glycol) with carbon dioxide in the presence of a homogeneous carbonation catalyst in a first reaction zone to provide a crude cyclic carbonate stream containing cyclic carbonate (ethylene carbonate in the case of dimethyl carbonate and ethylene glycol) and homogeneous carbonation catalyst; and reacting at least a portion of the cyclic carbonate (e.g. ethylene carbonate) from the crude cyclic carbonate stream with an aliphatic monohydric alcohol (methanol in the case of dimethyl carbonate and ethylene glycol), in a second reaction zone in the presence of a heterogeneous transesterification catalyst to provide a crude product stream containing a dialkyl carbonate (e.g. dimethyl carbonate) and diol (e.g. ethylene glycol).

Optionally, either aspect may contain the step of recovering the dialkyl carbonate and the diol from the crude product stream.

Preferably, the alkylene oxide is of formula (I):

wherein $R_1$ and $R_2$ independently of one another denote a divalent group represented by the formula $—(CH_2)_m—$, wherein m is an integer from 1 to 3, which is unsubstituted or substituted with at least one substituent selected from the group consisting of $C_1$–$C_{10}$ alkyl group and a $C_6$–$C_{10}$ aryl group, wherein $R_1$ and $R_2$ can share the same substituent; and the aliphatic monohydric alcohol is of the formula:

$$R_3—OH \qquad (II)$$

wherein $R_3$ is a monovalent aliphatic $C_1$–$C_{12}$ hydrocarbon group which is unsubstituted or substituted with at least one substituent selected from the group consisting of a $C_1$–$C_{10}$ alkyl group and a $C_6$–$C_{10}$ aryl group.

The present invention provides the advantage of continuously producing dialkyl carbonates and diols, such as dimethyl carbonate and ethylene glycol, with relatively high yield and selectivity to the desired dialkyl carbonate and diol, and obtaining the productivity and economic benefits associated with integrating the carbonation and transesterification processes.

Additional objects, advantages and novel features of the invention will be set forth in part in the description and examples which follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENT

The present invention is a continuous integrated process for preparing dialkyl carbonates and diols from alkylene oxides, carbon dioxide and aliphatic monohydric alcohols.

In preparing the dialkyl carbonates and diols, an alkylene oxide is first reacted with $CO_2$ in the presence of a homogeneous carbonation catalyst to provide a corresponding cyclic carbonate. Preferably, the alkylene oxide is represented by structural formula (I) above. Examples of such alkylene oxides include ethylene oxide, propylene oxide, styrene oxide, trimethylene oxide, cyclohexene oxide, and the like. Of these alkylene oxides, ethylene oxide and propylene oxide are preferably used because of their good availability and high demand end products. Ethylene oxide is most preferably used. The alkylene oxide feed may contain various impurities, especially the impurities resulting from its manufacture. For instance, ethylene oxide which is made by selective oxidation of ethylene may contain carbon dioxide, water and aldehydes.

The first carbonation reaction involving this preferred alkylene oxide may be represented by the following:

(III)

wherein $R_1$ and $R_2$ independently of one another denote a divalent group represented by the formula $-(CH_2)_m-$, wherein m is an integer from 1 to 3, which is unsubstituted or substituted with at least one substituent selected from the group consisting of $C_1-C_{10}$ alkyl group and a $C_6-C_{10}$ aryl group, wherein $R_1$ and $R_2$ can share the same substituent.

The carbon dioxide to be employed can contain inert gases, such as nitrogen, hydrogen, carbon monoxide and lower hydrocarbons, and can originate from natural sources or industrial gases or waste gases. The water content of the carbon dioxide is preferably below 1 mol %, and the concentration of sulfur is preferably below 100 ppm by weight.

The content and amount of carbon dioxide will depend on the reaction rate, reactor type and specific catalyst used, and is adjusted to maximize the economics of the process. Preferably, the molar ratio of alkylene oxide to carbon dioxide is about 1:1, but an excess of carbon dioxide is also contemplated. Therefore, according to the present invention, the molar ratio of alkylene oxide to carbon dioxide is preferably in the range from about 1:0.9 to 1:15 and more preferably in the range from about 1:1 to 1:3.

In the first aspect of the present invention a homogeneous carbonation catalyst is used in both reaction zones of the process. In the first reaction zone of the first aspect, the reactants (i.e., alkylene oxide and carbon dioxide) are contacted in the presence of a homogeneous catalyst. The homogeneous carbonation catalyst is preferably a neutral or basic homogeneous carbonation catalyst which provides adequate reaction kinetics for both the carbonation reaction and transesterification reaction. More preferably, the homogeneous carbonation catalyst contains a basic component and a halide containing component, wherein the basic component is selected from the group consisting of carbonates, bicarbonates, acetates, amines, phosphines and mixtures thereof and the halide containing component is selected from the group consisting of alkali halides, quaternary ammonium halides and mixtures thereof. Examples of suitable homogeneous catalysts include an alkali or quaternary ammonium halide; basic materials, preferably selected from an alkali, alkali earth, transition metal or quaternary ammonium carbonate, bicarbonate, hydroxide or acetate; an organic amine or phosphine; or mixtures of these materials.

The specific catalyst is chosen to optimize the economics of the overall integrated process and will depend upon the particular alkylene oxide being reacted and the reaction conditions. For example, it is contemplated that potassium iodide, tetraethyl ammonium bromide and mixtures of potassium iodide or tetraethyl ammonium bromide with a mild base, such as sodium bicarbonate are particularly effective for the synthesis of ethylene carbonate, dimethyl carbonate and ethylene glycol. The catalyst can be introduced to the reactor as part of a recycle stream, the fresh feed, make-up or a combination of these. The amount of catalyst measured as the concentration of catalyst in the reactor effluent is generally about 0.05 to 5% by weight, preferably about 0.15 to 2.0% by weight.

In the first aspect, the carbonation reaction is preferably carried out in a continuous mode utilizing various reaction configurations, such as a stirred-tank, tubular, fixed or packed-bed reactor, in a single or multiple-reactor configuration, at from about 50° C. up to about 250° C., preferably between about 100° C. up to about 200° C. and more preferably between about 150° C. up to about 200° C., and at pressures ranging from about at least about 1379 kPa (200 psi) up to about 13790 kPa (2000 psi), preferably from about 2069 kPa (300 psi) up to about 8964 kPa (1300 psi) and more preferably from about 3448 kPa (500 psi) up to about 6895 kPa (1000 psi). In the preferred mode of operation, the reactor temperature and pressure are optimized to insure a relatively high conversion and selectivity to the desired alkylene carbonate. A provision for heat removal from the reactor is normally required, since the carbonation reaction is exothermic.

Preferably, the effluent from the carbonation reaction zone is fed into a second carbonation reaction zone that can operate under different conditions or a different configuration to provide a greater overall conversion of the alkylene oxide, preferably greater than 90% overall conversion. Preferably, the second carbonation reaction zone is a separate tubular polishing reactor which operates at from about 50° C. up to about 250° C., preferably between about 100° C. up to about 200° C. and at pressures ranging from at least about 1379 kPa (200 psi) up to about 13790 kPa (2000 psi), preferably from about 2069 kPa (300 psi) to about 8964 kPa (1300 psi).

Typically, impurities are formed in the carbonation reaction in the form of by-products. Glycols may be formed along with the alkylene carbonates, especially if there is water present in the system. For example, by reacting ethylene oxide with $CO_2$ to produce ethylene carbonate, typically ethylene glycol and some higher molecular weight glycols are produced.

The carbonation reactor effluent, either from the first carbonation reaction zone or from the second carbonation reaction zone (if used), is preferably subjected to a flash separation to remove the volatiles, such as unreacted $CO_2$ and alkylene oxide.

The effluent from the carbonation reaction is preferably not subjected to any further separation. Thus, the cyclic carbonate and the by-product impurities produced in the carbonation reaction, along with the homogeneous catalyst, are then fed to the transesterification reactor, where the cyclic carbonate is reacted with an aliphatic monohydric alcohol in the presence of the homogeneous carbonation catalyst to provide a corresponding dialkyl carbonate and diol.

Preferably, the aliphatic monohydric alcohol is represented by structural formula (II) above and has a boiling point lower than that of the produced diol. The type of an aliphatic monohydric alcohol which can be used in the present invention varies depending on the particular cyclic carbonate produced by the carbonation reaction. Examples of such aliphatic monohydric alcohols include methanol, ethanol, n-propanol, iso-propanol, alkyl alcohol, butanol (including isomers of butanol), 3-butene-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers), and the like. The above mentioned aliphatic monohydric alcohol may be substituted with at least one substituent, such as a halogen atom, a lower alkoxy group, a cyano group, an alkoxycarbonyl group, an aryloxycarbonyl group, an acyloxy group, a nitro group or the like.

Of the aliphatic monohydric alcohols, an alcohol having 1 to 6 carbon atoms is preferably used. When ethylene carbonate is the cyclic carbonate, an alcohol having 1 to 4 carbon atoms, i.e., methanol, ethanol, propanol (isomers) or butanol (isomers) is preferably used. The method of the present invention can be employed advantageously especially when methanol and ethylene carbonate are used as feedstocks for the transesterification reaction.

According to the present invention, it has now been found that it is unnecessary to purify the cyclic carbonate or separate the homogeneous carbonation catalyst to achieve relatively high yields and selectivity to the desired dialkyl carbonate and diol, resulting in significant economic benefits and advantage due to the elimination of the separation and purification steps, e.g., one or more evaporators and two vacuum distillation columns, previously thought necessary. In addition to lower operating and capital costs associated with eliminating these steps, a yield benefit is realized by eliminating losses of cyclic carbonate attributable to the separation and purification steps.

As such, an integrated process is provided which produces both a dialkyl carbonate and a diol with high productivity. In accordance with the present invention, the term "productivity" means the yield per unit volume of both the carbonation and transesterification zones per unit time, i.e., the space time yield for the overall integrated process.

This transesterification reaction may be represented by the following:

(IV)

wherein $R_1$ and $R_2$ independently of one another denote a divalent group represented by the formula $-(CH_2)_m-$, wherein m is an integer from 1 to 3, which is unsubstituted or substituted with at least one substituent selected from the group consisting of $C_1-C_{10}$ alkyl group and a $C_6-C_{10}$ aryl group, wherein $R_1$ and $R_2$ can share the same substituent; and $R_3$ is a monovalent aliphatic $C_1-C_{12}$ hydrocarbon group which is unsubstituted or substituted with at least one substituent selected from the group consisting of a $C_1-C_{10}$ alkyl group and a $C_6-C_{10}$ aryl group. Other components in the feed to the transesterification reactor may include various other species, commonly hydroxyalkyl carbonates and dialkyl carbonates, as fresh feed or in one or more recycle streams.

The reactants to the transesterification reaction (i.e., the cyclic carbonate and the aliphatic monohydric alcohol) are contacted in the presence of the homogeneous carbonation catalyst from the carbonation reaction. The transesterification reaction is preferably carried out in a continuous mode utilizing various reactor configurations, such as, stirred-tank or tubular reactors, in a single or multiple-reactor configuration, or a reactive distillation column, at from about 50° C. up to about 250° C., preferably between about 75° C. up to about 170° C., and at pressures ranging from about atmospheric pressure up to about 13790 kPa (2000 psi), preferably from about 138 kPa (20 psi) up to about 2069 kPa (300 psi). In the preferred mode of operation, the reactor temperature and pressure are optimized to insure a relatively high conversion and selectivity to the desired dialkyl carbonate and diol and to optimize the economics of the overall integrated process. Generally, a reactive distillation column will tend to give higher conversions of ethylene carbonate and methanol.

In the second aspect of the present invention a homogeneous carbonation catalyst is used in the first carbonation reaction zone and a heterogeneous transesterification catalyst is used in the second transesterification reaction zone. This aspect is similar to the first aspect except for the following process conditions which are preferred for the two catalyst process of the second aspect of the present invention.

In the second aspect, the reactants (i.e., alkylene oxide and carbon dioxide) are contacted in the presence of a homogeneous carbonation catalyst. In the second aspect of the present invention (i.e., the homogeneous-heterogeneous catalyst process) the carbonation catalyst can typically be any homogeneous catalyst known in the art which provides adequate reaction kinetics. Preferred homogeneous carbonation catalysts include phosphonium halides, arsonium halides, quaternary ammonium halides and alkali halides.

The specific homogeneous carbonation catalyst is chosen to optimize the economics of the overall integrated process and will depend upon the particular alkylene oxide being reacted and the reaction conditions. For example, in the second aspect it is contemplated that alkali-metal halides, such as KI or quaternary ammonium halides, are particularly effective for the synthesis of the ethylene carbonate. Additionally, alkali-earth and transition metal halides, as well as carbonates and bicarbonates of alkali, alkali-earth and transition metals, alone or in combination, are effective for the synthesis of ethylene carbonate. The homogeneous catalyst can be introduced to the reactor as part of a recycle stream, the fresh feed, make-up or a combination of these. The amount of homogeneous catalyst measured as the concentration of catalyst in the reactor effluent is generally about 0.05 to 5% by weight, preferably about 0.15 to 2.0% by weight.

In the second aspect, the carbonation reaction is preferably carried out in a continuous mode utilizing various reaction configurations, such as a stirred-tank, tubular, fixed or packed-bed reactor, in a single or multiple-reactor configuration, at from about 50° C. up to about 250° C., preferably between about 100° C. up to about 200° C., and at pressures ranging from about atmospheric pressure up to about 13790 kPa (2000 psi), preferably from about 2069 kPa ( 300 psi) up to about 8964 kPa ( 1300 psi). In the preferred mode of operation, the reactor temperature and pressure are optimized to insure a relatively high conversion and selectivity to the desired alkylene carbonate. A provision for heat removal from the reactor is normally required, since the carbonation reaction is exothermic.

Preferably, the effluent from the carbonation reaction zone of the second aspect is fed into a second carbonation reaction zone that can operate under different conditions or a different configuration to provide a greater overall conversion of the alkylene oxide, preferably greater than 90% overall conversion. Preferably, the second carbonation reaction zone is a separate tubular polishing reactor which operates at from about 50° C. up to about 250° C., preferably between about 100° C. up to about 200° C. and at pressures ranging from about atmospheric up to about 13790 kPa (2000 psi), preferably from about 2069 kPa (300 psi) to about 8964 kPa (1300 psi).

According to the second aspect of the present invention, it has now been found that it is unnecessary to purify the cyclic carbonate or separate the homogeneous carbonation catalyst to achieve relatively high yields and selectivity to the desired dialkyl carbonate and diol, resulting in significant economic benefits and advantage due to the elimination of the purification steps, e.g., one or more evaporators and two vacuum distillation columns, previously thought necessary. In addition to lower operating and capital costs associated with eliminating the purification steps, a yield benefit is realized by eliminating losses of cyclic carbonate attributable to the purification steps. Moreover, the transesterification reaction, with both the heterogeneous and homogeneous catalysts present, can generally be operated at a higher space velocity, relative to the heterogeneous transesterification catalyst, than a process which recovers the homogeneous carbonation catalyst prior to the transesterification reaction. As such, an integrated process is provided which produces both a dialkyl carbonate and a diol with high productivity. In accordance with the present invention, the term "productivity" means the yield per unit volume of both the carbonation and transesterification zones per unit time, i.e., the space time yield for the overall integrated process.

In the second aspect, the reactants to the transesterification reaction (i.e., the cyclic carbonate and the aliphatic monohydric alcohol) are contacted in the presence of a heterogeneous transesterification catalyst. The transesterification catalyst can typically include any heterogeneous catalyst known in the art which provides adequate reaction kinetics in the presence of the homogeneous carbonation catalyst and minimizes side reactions with the impurities contained in the cyclic carbonate. Examples of such catalysts include ion-exchangers, such as, anion-exchange resins having tertiary amino groups, amide groups, or at least one type of ion-exchange group selected from the group consisting of sulfonate, carboxylate and phosphate groups; strongly basic solid anion-exchangers having quarternary ammonium groups as ion-exchange groups and the like; inorganic metal oxides; solid inorganic compounds, such as, silica, alumina, magnesia and transitional aluminas, such as, pseudoboehmite, silica-alumina, silica-magnesia, aluminosilicate, gallium silicate, various types of zeolites various types of metal-exchanged zeolites, ammonium-exchanged zeolites, inorganic solid support catalysts containing metals; and the like. The term "transitional" means it is not fully calcined.

Preferred transesterification catalysts used in the second aspect include anion exchange resins having tertiary amine, quaternary ammonium, sulfonic acid or carboxylic acid functional groups; solid inorganic compounds, such as, alumina or pseudoboehmite; solid support catalysts containing alkaline earth metal halides, such as, those described in U.S. Pat. No. 5,498,743, which is incorporated herein by reference; or inorganic solid support catalysts containing ions, metals, compounds or complexes of at least one element of Groups 1, 2, 4–10, 12 and 13–17 (IUPAC classification, previously Groups 1A, 2A, 4B–8B, 2B and 3A–7A) of the Periodic Table.

The specific heterogeneous catalyst is chosen to optimize the economics of the overall integrated process and will depend upon the particular cyclic carbonate and aliphatic monohydric alcohol reacted, the specific homogeneous carbonation catalyst, the type and amount of impurities contained in the cyclic carbonate and the transesterification reaction conditions. For example, it is contemplated that pseudoboehmite (AlO—OH) and magnesia (MgO) are particularly effective as a transesterification catalysts for the synthesis of dimethyl carbonate and ethylene glycol in accordance with the present invention. The weight hourly space velocity (WHSV) will typically be from about 0.1 to about 10 hr$^{-1}$, preferably 0.5 to about 2 hr$^{-1}$.

The transesterification reaction of the second aspect is preferably carried out in a continuous mode utilizing various reactor configurations, such as, fixed or packed-bed reactors, in a single or multiple-reactor configuration, or a reactive distillation column, at from about 50° C. up to about 250° C., preferably between about 75° C. up to about 140° C., and at pressures ranging from about atmospheric pressure up to about 13790 kPa (2000 psi), preferably from about 138 kPa (20 psi) up to about 2069 kPa (300 psi). In the preferred mode of operation, the reactor temperature and pressure are optimized to insure a relatively high conversion and selectivity to the desired dialkyl carbonate and diol and to optimize the economics of the overall integrated process. Generally, a reactive distillation column will tend to give higher conversions of ethylene carbonate and methanol, while a packed-bed reactor offers flexibility in handling various heterogeneous catalysts.

Figure 1:
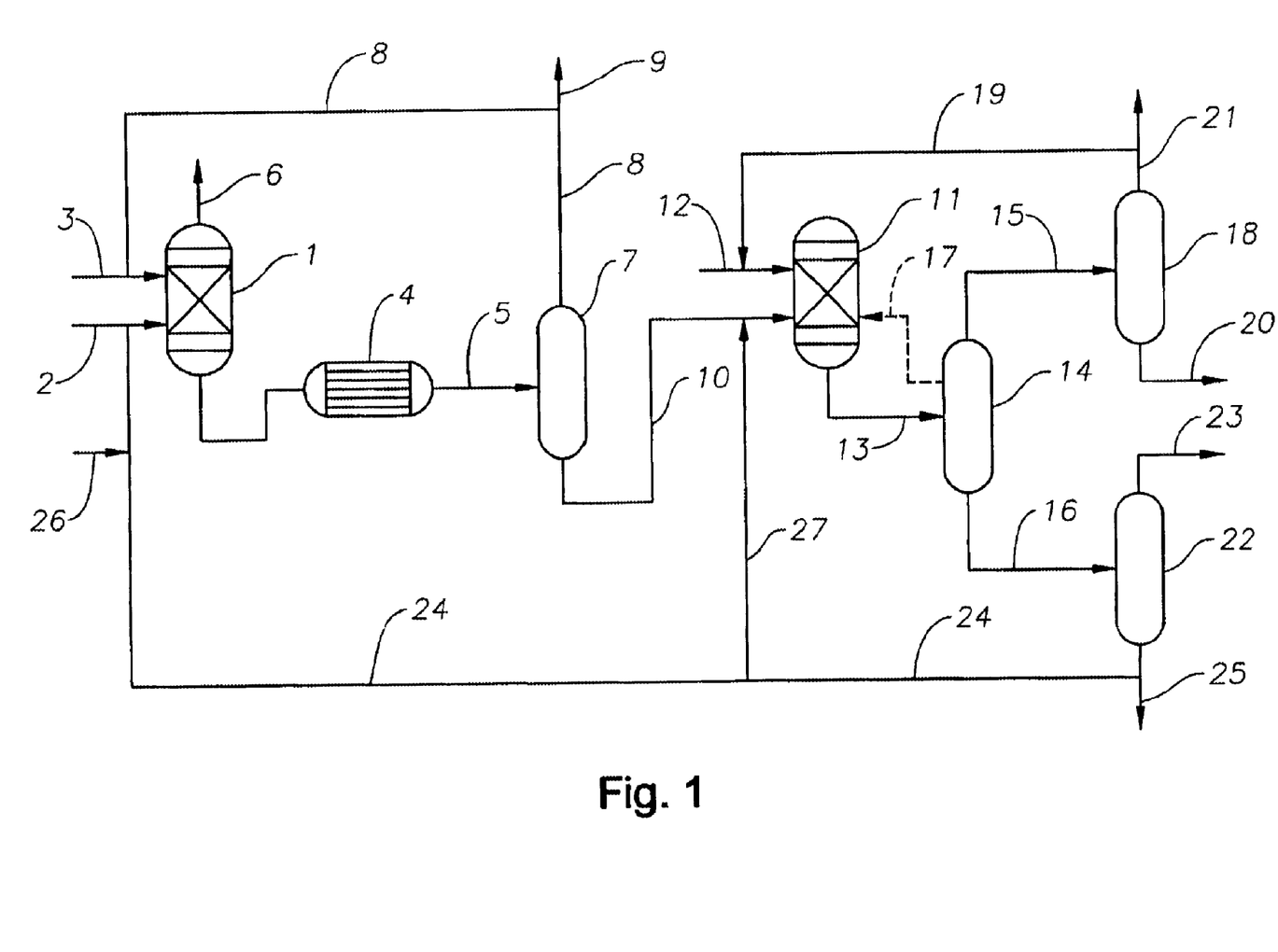
FIG. 1 is a schematic of a preferred embodiment of the integrated process, which utilizes a circulating homogeneous catalyst.

The first embodiment of the integrated process, which utilizes a circulating homogeneous catalyst, is shown schematically in FIG. 1. Equipment not essential to the understanding of the invention, such as, heat exchangers, pumps, compressors and the like are not shown.

Referring now to FIG. 1, the carbonation reactor 1 is preferably a stirred tank reactor in which the alkylene oxide is reacted with $CO_2$ to form alkylene carbonate. The reactor 1 is charged with alkylene oxide, catalyst and recycled ethylene carbonate via line 2 and with $CO_2$ via line 3. It is should be noted that the catalyst is mainly dissolved in the recycled ethylene carbonate, with a temporarily high local concentration of ethylene oxide. In the case of ethylene carbonate, the reaction of ethylene oxide and $CO_2$ is exothermic and the temperature of the reaction zone is usually maintained below about 250° C. and the pressure is maintained in the range from about 500 to about 1000 psia to enhance product quality, yield and selectivity. Preferably, the reaction temperature is between about 150° C. and 200° C. The molar ratio of $CO_2$ to ethylene oxide is generally maintained at about 1.3:1 to 1:1, preferably 1.15:1 to 1.05:1. Preferably, the effluent from reactor 1 is fed to a tubular polishing reactor 4, to obtain greater than 90% overall conversion of the alkylene oxide.

The carbonation reactor effluent is withdrawn from reactor 4 via line 5. The carbonation reactor effluent 5 contains cyclic carbonate, unreacted $CO_2$, a small amount of unreacted alkylene oxide, homogeneous catalyst, and by-product impurities, such as, mono- and poly-glycols. Also provided on reactor 1 is vent line 6 which can be operated continuously or intermittently to purge the reactor of volatile impurities which could unfavorably affect product quality. For example, in the case of ethylene carbonate synthesis from ethylene oxide and $CO_2$, acetaldehyde is formed which, if it remained in the reaction mixture, could initiate side reactions to form unwanted polymeric materials or other byproducts that could unfavorably affect product quality.

The carbonation reactor effluent is fed from line 5 into separator 7 from which $CO_2$ and unreacted alkylene oxide is separated as a gaseous effluent and, optionally, returned to the carbonation reactor 1 via lines 8 and 3. A purge line 9 is also provided to vent some or all of the overhead gas from separator 7. Separator 7 is preferably a simple flash unit. In the case of ethylene carbonate the reactor effluent is flashed at pressures ranging from about 0.5 up to about 30 psia and temperatures between about 120 and 200° C. The liquid effluent will typically contain about 0.1 to 5 wt % catalyst, about 0.3 to 20 wt % polyglycols, about 0.2 to 20 wt % mono-ethylene glycol and about 90 to 99 wt % ethylene carbonate.

The liquid effluent from separator 7 is passed via line 10 into a transesterification reactor 11, which is preferably a tubular reactor or a stirred tank followed by a tubular section. An aliphatic monohydric alcohol is also fed to transesterification reactor 11 via line 12. The molar ratio of alcohol to cyclic carbonate fed to reactor 11 is generally from about 2:1 to about 6:1, preferably about 3:1 to about 4:1. In the case of dimethyl carbonate and ethylene glycol, the reaction of ethylene carbonate and methanol will be maintained at a temperature of about 80 to 200° C., preferably about 100 to 150° C., and pressures about 690 kPa (100 psi) to 2069 kPa (300 psi). The conversion per pass of ethylene carbonate to dimethyl carbonate is about 30 to 70%, preferably about 50 to 70%, most preferably about 50 to 65%.

The transesterification reactor effluent is withdrawn from reactor 11 via line 13. The transesterification reactor effluent 13 will typically contain dialkyl carbonate, a diol, unreacted cyclic carbonate, unreacted alcohol, homogeneous catalyst and by-products, such as, organic oxygenates and polyglycols. However, the composition, and by-product yields in particular, can vary widely based upon the specific catalyst and operating conditions employed.

The transesterification reactor effluent is fed from line 13 into a distillation column 14, where an overhead product stream containing the dialkyl carbonate, alcohol and organic oxygenates is removed via line 15 and a bottoms product stream containing the diol, cyclic carbonate, homogeneous catalyst and polyglycols is removed via line 16. In the case of dimethyl carbonate and ethylene glycol, the distillation column is typically operated at a pressure of between about 5 and 30 psia and a temperature range at the top of the column of about 50 to 90° C. Optionally, a side-stream 17 is withdrawn from column 14, which is depleted of the diol and cyclic carbonate, and recycled to transesterification reactor 11 to reduce the load on dialkyl carbonate product distillation column 18.

Figure 4:
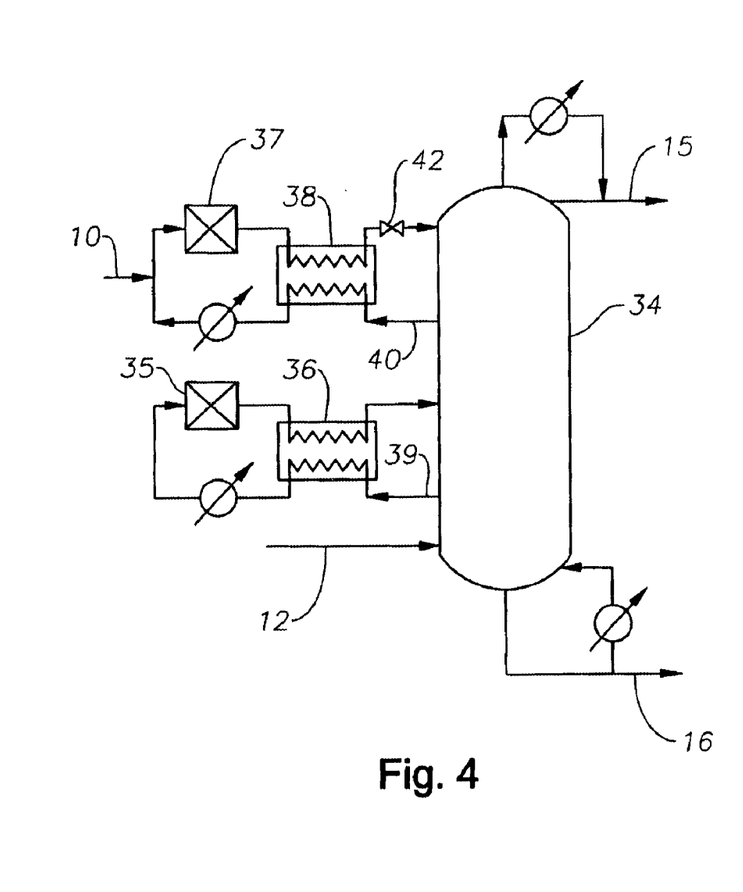
FIG. 4 is a schematic representation of a transesterification distillation tower with upper and lower external reaction zones with integrated heat exchangers at each reaction zone.
Figure 5:
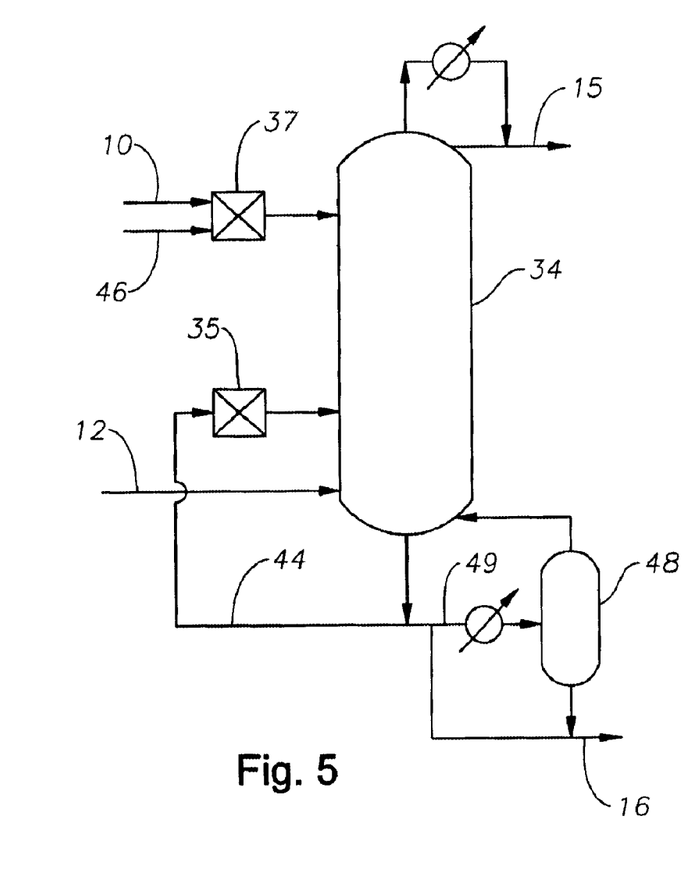
FIG. 5 is a schematic representation of a transesterification distillation tower with upper and lower external reaction zones having a bottoms recycle assembly.

Alternatively, as shown in FIGS. 4 and 5, transesterification reactor 11 and distillation column 14 can be replaced with a single distillation tower 34 comprising a plurality of reaction zones 35 and 37 communicating with a plurality of heat exchangers 36 and 38 via conduits 39 and 40, respectively. Such a configuration allows reaction zones 35 and 37 to operate at different temperatures than distillation tower 34. With the addition of a pressure reducing device 42, reaction zone 37 can also operate at a different pressure.

FIG. 5 depicts another embodiment using distillation tower 34 wherein the bottoms are recycled via conduit 44 and reaction zone 35 to a lower portion of distillation tower 34. The upper reaction zone 37 is a once through process wherein alkylene carbonate (e.g., ethylene carbonate) is fed via conduit 10 and an alkanol (e.g., methanol) is feed via conduit 46. Bottoms can also be transported to knock-out drum 48 via conduit 49, wherein the vapor from knock-out drum 48 is recycled to tower 34 and the bottoms of knock-out drum 48 sent via conduit 16 for subsequent downstream treatment. The configurations shown in FIGS. 4 and 5 can allow greater conversion of alkylene carbonate than would be obtained in a single reactor.

The overhead product stream is fed via line 15 to dialkyl carbonate product distillation column 18, where the alcohol is taken overhead and recycled via lines 19 and 12 to transesterification reactor 11 and dialkyl carbonate product is removed from the bottom of reactor 11 via line 20 and sent to storage. A purge stream 21 is also provided to prevent the accumulation of light by-product impurities. In the case of a dimethyl carbonate, the dialkyl carbonate product distillation column 18 is typically operated at a pressure of about 828 kPa (120 psia) to 1379 kPa (200 psia) and a temperature range for about 120 to 190° C. Dimethyl carbonate and methanol form a low-boiling azeotrope, so that the overhead stream includes up to about 15 wt %, and typically about 5–15 wt %, dimethyl carbonate. This dimethyl carbonate is recycled to transesterification reactor 11 along with the methanol via conduits 21, 19 and 12.

The bottoms product stream from distillation column 14 is fed via conduit 16 to diol product distillation column 22, where the diol product is removed overhead via conduit 23 and sent to storage or further processing, and a bottoms stream containing unreacted cyclic carbonate, homogeneous catalyst, polyglycols and other heavies is removed via conduit 25. Optionally, the diol product which is taken overhead via conduit 23 may be withdrawn from an intermediate point in column 22, and the overhead product from column 22 is returned to an intermediate feed point in column 14. A hydrolysis reactor can also be incorporated into the integrated process to provide a highly purified diol, e.g., ethylene glycol. The feed to this hydrolysis reactor can include the diol product stream, which may contain small amounts of cyclic carbonate, and some or all of the unreacted cyclic carbonate containing stream, that is otherwise recycled to the transesterification reactor. Water is also fed to the hydrolysis reactor to convert cyclic carbonate to diol with the formation of $CO_2$ by-product. In the case of ethylene glycol, distillation column 22 is operated in a temperature range of about 100 to 170° C., under a vacuum in the range of about 50 to 200 mm Hg. A portion of this bottoms stream is recycled to the carbonation reactor 1 via conduits 24 and 2. Purge conduit 25 is provided to prevent accumulation of polyglycols and other heavies. The heavies stream from purge conduit 25 may be subjected to vacuum evaporation or distillation to recover valuable ethylene carbonate. Make-up and recycled homogeneous catalyst is fed via conduits 26 and 24, respectively, into conduit 2. A portion of the bottoms stream is also recycled to the transesterification reactor 11 via lines 24, 27, and 10. The proportion of the bottoms stream which is recycled to each reactor 1 and 11 will be chosen to optimize the economics of the process and will depend upon the specific dialkyl carbonate and diol being produced.

In another embodiment, at least a portion of the bottoms stream from diol product distillation column 22 can be fed to an evaporator (not shown) from which a cyclic carbonate-rich stream is recovered as a vaporous effluent and recycled to transesterification reactor 11. In the case of ethylene carbonate, the operating conditions of the evaporator typically include temperatures in the range of about 120 to 180° C., under a vacuum in the range of about 10 to 80 mm Hg. A liquid effluent stream from the evaporator, rich in homogeneous catalyst, is also recovered and recycled to carbonation reactor 1.

The second embodiment of the integrated process, which utilizes a circulating homogeneous carbonation catalyst and a heterogeneous transesterification catalyst, is accomplished as described above with reference to FIG. 1, however the second aspect includes several process condition modifications. The foregoing description of FIG. 1 applies equally to the description of FIG. 2 except that the following process condition modifications are specific to the homogeneous carbonation catalyst—heterogeneous transesterification catalyst process depicted in FIG. 2.

Figure 2:
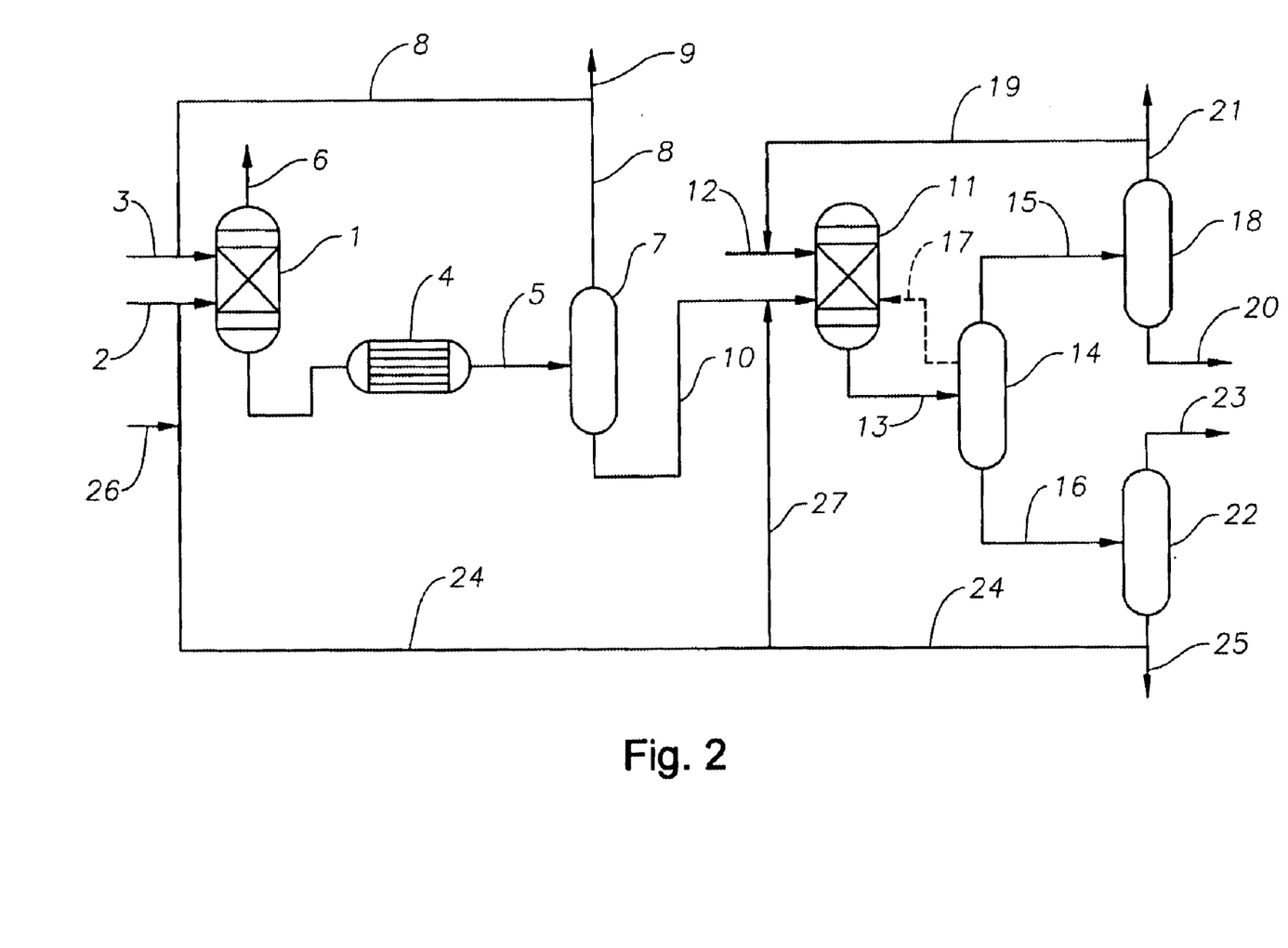
FIG. 2 is a schematic of an embodiment of the integrated process, which utilizes a circulating homogeneous carbonation catalyst and a heterogeneous transesterification catalyst.

Referring now to FIG. 2, as in the first aspect, reactor 1 is charged with alkylene oxide and catalyst via conduit 2 and with $CO_2$ via conduit 3. In the case of ethylene carbonate, the reaction of ethylene oxide and $CO_2$ is exothermic and the temperature of the reaction zone in the second aspect of the invention is usually maintained below about 220° C. and the pressure is maintained in the range from about 3448 kPa (500 psi) to about 6897 kPa (1000 psi) to enhance product quality. Preferably, the reaction temperature is between about 180° C. and 200° C.

In the second aspect, the liquid effluent from separator 7 is passed via conduit 10 into transesterification reactor 11, which is preferably a fixed bed reactor. The WHSV in the fixed bed reactor of the second aspect is generally about 0.3 to 3 $hr^{-1}$.

As in the first aspect, a hydrolysis reactor can also be incorporated into the integrated process of the second aspect to provide a highly purified diol, e.g., ethylene glycol. The feed to this hydrolysis reactor can include the diol product stream, which may contain small amounts of cyclic carbonate, and some or all of the unreacted cyclic carbonate containing stream, that is otherwise recycled to the transesterification reactor. Water is also fed to the hydrolysis reactor to convert cyclic carbonate to diol with the formation of $CO_2$ by-product.

Figure 3:
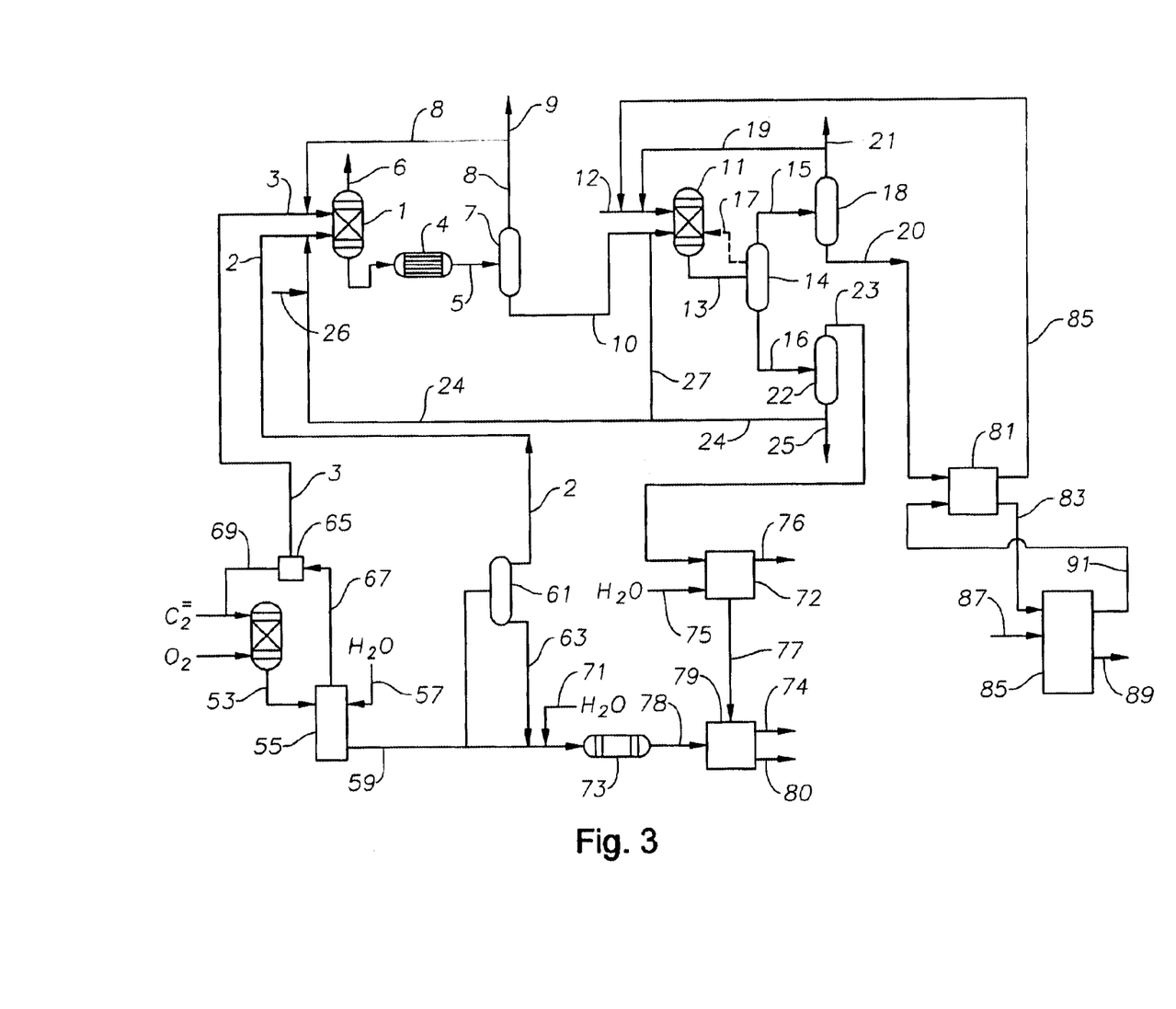
FIG. 3 is a schematic representation of a reaction process for the production of polycarbonate from ethylene utilizing the integrated process according to FIGS. 1 and 2 above.

Use of the integrated process of all aspects of the present invention for the production of dimethyl carbonate and ethylene glycol is particularly well suited for incorporation into an ethylene glycol plant, which produces ethylene glycol from ethylene, oxygen and water by the method described in the Encyclopedia of Chemical Processing and Design, J. J. McKetta, Marcel Dekker, Inc., N.Y., P. 237 to 243 (1984), which is incorporated herein by reference. Such a process is depicted in FIG. 3, wherein ethylene is first reacted with oxygen in a selective oxidation reactor 51 to produce ethylene oxide, $CO_2$ and water (i.e., a gas mixture) which are removed from reactor 51 via conduit 53. This gas mixture typically includes unconverted ethylene and one or more relatively insert 'ballast' components, such as, methane. The gas mixture containing ethylene oxide is fed via conduit 53 to absorber unit 55 where it is contacted with $H_2O$ fed via conduit 57, to absorb most of the ethylene oxide in the water. The ethylene oxide in water is taken as bottoms from absorber unit 55 via conduit 59 to distillation column 61 wherein ethylene oxide is taken overhead from column 61 via conduit 2 and fed to carbonation reactor 1 as discussed above in FIG. 1, and $H_2O$, ethylene glycol, polyglycols and residual ethylene oxide are removed as bottoms via conduit 63 to join the fed to hydration reactor 73. Additional water 71 may be added to the feed of hydration reactor 73, to adjust the water to ethylene oxide ratio to a preferred range of between about 10:1 to 30:1. Hydration reactor 73 preferably contains no catalyst, and operates at 120° C. to 250° C. and pressure sufficient to keep the components in the liquid phase. Products from hydration reactor 73 are taken via conduit 78 to glycol separations unit 79, which removes water and produces an ethylene glycol product stream 74, and residual polyglycol stream 80. Optionally, the various polyglycols, such as, ethylene glycol and triethylene glycol, may be produced as separate product streams.

The diol product stream from column 22, which may contain up to about 20% by weight ethylene carbonate, is taken via conduit 23 to hydrolysis unit 72. $H_2O$ is added to this unit, and most of the ethylene carbonate entering the unit is hydrolyzed to ethylene glycol, which is removed via conduit 77, and to $CO_2$, which is removed via conduit 76. This $CO_2$ may, optionally, be recycled to carbonation reactor 1.

The overhead from absorber unit 55 which includes ethylene, $CO_2$ and ballast gas is fed to $CO_2$ separation unit 65 via conduit 67 wherein $CO_2$ is taken overhead from $CO_2$ separation unit 65 via conduit 71 wherein it is either released to the atmosphere or fed to carbonation reactor 1 via conduit 3, and residual gas taken via conduit 69 is recycled to selective oxidation reactor 51.

The removed ethylene oxide can be returned as ethylene glycol, essentially on a 1:1 mole basis. Moreover, since the ethylene glycol produced in accordance with the present invention is primarily mono-ethylene glycol, the amount of ethylene oxide that becomes mono-ethylene glycol as opposed to polyethylene glycols can be actually greater via the integrated process than by the ethylene glycol plant. As such, the ethylene glycol, having a higher percentage of mono-ethylene glycol, can be returned to the ethylene glycol plant just prior to the purification equipment, reducing the amount of glycol purification required for the volume returned. This is especially beneficial for the production of fibergrade mono-ethylene glycol, which has a minimum purity specification of 99.9 wt % mono-ethylene glycol.

Substantially pure dialkyl carbonate (e.g., dimethyl carbonate) is taken as bottoms via conduit 20 from distillation column 18 and fed, for example, into diphenyl carbonate production unit 81 having at least one reactor with metal-containing catalyst operating at 80–300° C. and 2–4,000 kPa, and having associated separation devices. This diphenyl carbonate production unit 81 produces diphenyl carbonate and methanol. The methanol is taken overhead via conduit 85 and recycled via conduit 12 to transesterification reactor 11. The diphenyl carbonate is removed from diphenyl carbonate production unit 81 as bottoms stream via conduit 83. The diphenyl carbonate is thereafter reacted within polycarbonate reactor 85 with bisphenol-A, thereby producing polycarbonate and phenol. The polycarbonate is removed as a sidestream via conduit 89 and sent to storage, and the phenol is taken overhead via conduit 91 and recycled to diphenyl carbonate production unit 81.

It is contemplated that the unique integrated process for producing dialkyl carbonate from alkylene and an oxygen-containing gas can be used cost effectively produce commercial quantities of other products, such as, furazolidone, agrochemical/pharmaceutical intermediates, allyl diglycol carbonate (e.g., eye glass lenses), linear alkylcarbonate lubricants, oligocarbonate, light emitting diodes for outdoor display panels and gasoline octane improver.

EXAMPLES

The following examples have been carried out to illustrate preferred embodiments of the invention. These examples include reacting ethylene carbonate (EC) with methanol (MeOH) in an autoclave reactor in the presence of a pseudo-boehmite (AlO—OH) heterogeneous catalyst, repeating the reaction in the presence of a KI homogeneous catalyst and a tetraethyl ammonium bromide ($Et_4NH_4Br$) homogeneous catalyst, respectively, to simulate the transesterification reaction of the integrated process which circulates the homogeneous carbonation catalyst, and reacting EC and MeOH in a fixed bed tubular reactor in the presence of a MgO heterogeneous catalyst and a KI homogeneous catalyst. These examples also include the reaction of ethylene oxide with $CO_2$ in the presence of different homogeneous catalysts to form intermediate products containing ethylene carbonate and reacting the intermediate products with methanol to form dimethyl carbonate.

Example 1

Dimethyl carbonate (DMC) and ethylene glycol (EG) were prepared by reacting ethylene carbonate (EC) with methanol (MeOH) in the presence of a pseudoboehmite (AlO—OH) heterogeneous catalyst in a 300 ml autoclave reactor as follows: 5.0 grams of the AlO—OH catalyst were loaded into a 300 ml glass lined autoclave reactor with a Teflon®-coated stir bar. A feed containing 100 grams of a mixture of MeOH and EC, having a MeOH/EC molar ratio of 4:1, was added to the reactor. The reactor was maintained at 275° F. (135° C.) and 1724 kPa (250 psig) total pressure under constant mixing. After 4 hours the products were analyzed by standard GC techniques. The EC conversion was 23.9% with a DMC selectivity of 96.5% and an EG selectivity of 97.6%. The reactor conditions and results are listed in table 1 below.

Example 2

Example 1 was repeated, except that 2.0 grams of KI were added to the reactor along with the AlO—OH catalyst to simulate a circulating KI homogeneous carbonation catalyst. Although the KI is solid at room temperature, it dissolved in the liquid reaction mixture, so that it was homogeneous to the reaction mixture. After 4 hours the EC conversion was 52.8% with a DMC selectivity of 96.3% and an EG selectivity of 98.7%. The reactor conditions and results are listed in Table 1 below.

Example 3

Example 1 was repeated, except that 2.3 grams of $Et_4NH_4Br$ were added to the reactor along with the AlO—OH catalyst to simulate a $Et_4NH_4Br$ homogeneous carbonation catalyst. After 4 hours the EC conversion was 49.8% with a DMC selectivity of 99.3% and an EG selectivity of 98.5%. The reactor conditions and results are listed in Table 1 below.

TABLE 1

Results of Examples for Heterogeneous Transesterification catalyst with circulating Homogeneous carbonation catalyst.

| Example | 1 | 2 | 3 |
|---|---|---|---|
| Catalyst | AlO—OH | AlO—OH/KI | AlO—OH/$Et_4NH_4Br$ |
| Cat. Wt. (gms) | 5.0 | 5.0/2.0 | 5.0/2.3 |
| Temp. (° F.) | 275 | 275 | 275 |
| Press. (PSIG) | 250 | 250 | 250 |
| Rxn Time (hrs) | 4.0 | 4.0 | 4.0 |
| Feed Composition (wt %): | | | |
| MeOH | 59.2 | 59.2 | 59.2 |
| EC | 40.8 | 40.8 | 40.8 |
| MeOH/EC, Molar Ratio | 4.0 | 4.0 | 4.0 |
| Reaction Results: | | | |
| EC Conv. % | 23.9 | 52.8 | 49.8 |
| DMC Selec. % | 96.5 | 96.3 | 99.3 |
| EG Selec. % | 97.6 | 98.7 | 98.5 |

A review of Table 1 reveals that transesterification can proceed in the presence of the homogeneous halide-containing catalyst. Surprisingly, the presence of the homogeneous catalysts, in this example, actually significantly improved the conversion of EC and overall yield of both DMC and EG.

Example 4

Dimethyl carbonate (DMC) and ethylene glycol (EG) were prepared in the presence of a MgO heterogeneous catalyst. The MgO catalyst was utilized in a fixed-bed catalytic experiment as follows: 2.0 grams of an industrially prepared MgO material was loaded into a ⅜" tubular stainless steel reactor. The physical properties and composition of the MgO material are summarized in Table 2 below.

TABLE 2

Physical Properties of MgO catalyst

| Ash, wt % | BET Surface Area m$^2$/g | Al, ppm | Fe, ppm | Na, ppm | Ca, wt % |
|---|---|---|---|---|---|
| 95.7 | 145 | 280 | 680 | 540 | 0.64 |

A feed was prepared containing 53.5 wt % methanol (MeOH), 45.1 wt % ethylene carbonate (EC) and 1.4 wt % ethylene glycol (EG). 100 grams of the feed was mixed with 2 grams of KI to simulate the effluent of a carbonation reactor employing a KI homogeneous carbonation catalyst.

The mixture was passed over the MgO at 200 and 250° F. (93 and 121° C., respectively) at 1 LHSV. The reactor effluent at two temperatures is shown in Table 3.

TABLE 3

Conversion of Feed containing Ethylene Carbonate in the Presence of Methanol to DMC.

| Temperature (° F.) | 200 | 250 |
|---|---|---|
| Component (wt %): | | |
| MeOH | 45.0% | 43.5% |
| DMC | 14.0% | 19.7% |
| EG | 12.1% | 14.1% |
| EC | 26.4% | 21.3% |
| Other | 2.5% | 1.4% |

A review of Table 3 reveals that there was substantial conversion of the EC to the desired DMC and EG in the presence of a KI homogeneous carbonation catalyst.

Example 5

Dimethyl carbonate (DMC) was prepared by first reacting ethylene oxide (EO) with $CO_2$ in the presence of a tetraethyl ammonium bromide catalyst and then reacting the resulting intermediate product with methanol in a 300 ml autoclave reactor as follows: 30 grams of ethylene carbonate (EC), 1 gram of tetraethyl ammonium bromide and 41 grams of EO were loaded into a 300 ml stainless steel autoclave reactor.

The autoclave was pre-pressurized to 3348 kPa (500 psig) with carbon dioxide, and heated to 180° C. at about 3° C./minute. The temperature was held at 180° C. for about an hour. During this time, the pressure in the autoclave was maintained at about 4828 kPa (700 psig) by further addition of carbon dioxide. The autoclave was then cooled to about 50° C. The head space above the liquid product was vented and purged with nitrogen. About 3 grams of intermediate product was removed for sampling. Gas chromatography showed this intermediate product to consist of about 97% ethylene carbonate, showing that the ethylene oxide had mainly reacted with carbon dioxide to form ethylene carbonate.

To the remaining intermediate product was added 121 grams of methanol. The autoclave was sealed and heated to 120° C. for two hours. Gas chromatography indicated that the final product contained at least 20 grams of dimethyl carbonate.

Example 6

Dimethyl carbonate (DMC) was prepared by first reacting ethylene oxide (EO) with $CO_2$ in the presence of a potassium iodide catalyst and then reacting the resulting intermediate product with methanol in a 300 ml autoclave reactor as follows: 30 grams of ethylene carbonate (EC), 1 gram of potassium iodide (KI) and 38 grams of EO were loaded into a 300 ml stainless steel autoclave reactor.

The autoclave was pressurized to 3448 kPa (500 psig) with carbon dioxide, and heated to 180° C. at about 3° C./minute. The temperature was held at 180° C. for about an hour. During this time, the pressure in the autoclave was maintained at about 4828 kPa (700 psig) by further addition of carbon dioxide. The autoclave was then cooled to about 50° C. The head space above the liquid produce was vented and purged with nitrogen. About 1 gram of intermediate product was removed for sampling. Gas chromatography showed this intermediate product to consist of over 92% ethylene carbonate, again showing that the EO had mainly reacted with $CO_2$ to form EC.

To the remaining intermediate product was added 117 grams methanol. The autoclave was sealed and heated to 120° C. at 3° C./minute. The temperature was held at 120° C. for two hours, then cooled. Gas chromatography indicated that the final product contained at least 30 grams of dimethyl carbonate.

What is claimed is:

1. An integrated process for the production of a dialkyl carbonate and a diol from an alkylene oxide, carbon dioxide and an aliphatic monohydric alcohol comprising:
   (a) reacting an alkylene oxide with carbon dioxide in the presence of a homogeneous carbonation catalyst in a first reaction zone at a temperature in the range of about 50 to 250° C. and at a pressure of at least about 1379 kPa (200 psi) to provide a crude cyclic carbonate stream comprising a cyclic carbonate and homogeneous carbonation catalyst in an amount of 0.1 to 5 wt %;
   (b) directing said crude cyclic carbonate stream into a second reaction zone; and
   (c) reacting said cyclic carbonate with an aliphatic monohydric alcohol in said second reaction zone in the presence of said homogeneous carbonation catalyst to provide a crude product stream comprising a dialkyl carbonate and diol, wherein said crude cyclic carbonate stream has not been subjected to a separation other than to remove an amount of unreacted alkylene oxide, an amount of unreacted carbon dioxide, or both;
   wherein said homogeneous carbonation catalyst of (a) and (c) is a mixture comprising a halide containing component and a bicarbonate.

2. The process of claim 1, wherein said alkylene oxide is of the formula.

wherein $R_1$ and $R_2$ independently of one another denote a divalent group represented by the formula —$(CH_2)$m-, wherein m is an integer from 1 to 3, which is unsubstituted or substituted with at least one substituent selected from the group consisting of $C_1$–$C_{10}$ alkyl group and a $C_6$–$C_{10}$ aryl group, wherein $R_1$ and $R_2$ can share the same substituent; and said aliphatic monohydric alcohol is of the formula:

wherein $R_3$ is a monovalent aliphatic $C_1$–$C_{12}$ hydrocarbon group which is unsubstituted or substituted with at least one substituent selected from the group consisting of a $C_1$–$C_{10}$ alkyl group and a $C_6$–$C_{10}$ aryl group.

3. The process of claim 1, wherein said bicarbonate comprises sodium bicarbonate.

4. The process of claim 1, wherein said halide containing component is selected from the group consisting of: alkali halides, quaternary ammonium halides and mixtures thereof.

5. The process of claim 1, wherein said pressure is in the range of about 3448 kPa to 6897 kPa (500 to 1000 psig) and the temperature is in the range of about 150 to 200° C.

6. The process of claim 1, wherein the molar ratio of $CO_2$ to alkylene oxide is in the range from about 1.05 to 1.10 and the molar ratio of aliphatic monohydric alcohol to cyclic carbonate is in the range from about 2:1 to 6:1.

7. The process of claim 1, wherein said crude cyclic carbonate stream further comprises glycol impurities in an amount of up to 40% by weight, based upon total weight of said crude cyclic carbonate stream.

8. The process of claim 7, wherein said cyclic carbonate is ethylene carbonate, said aliphatic monohydric alcohol is methanol, and said glycol impurities comprise ethylene glycol and higher molecular weight glycols.

9. The process of claim 1, wherein said aliphatic monohydric alcohol contains dialkyl carbonate in an amount of up to 40% by weight, based upon the total weight of said aliphatic monohydric alcohol and said dialkyl carbonate.

10. The process of claim 1, further comprising a step of recovering said dialkyl carbonate and said diol from said crude product stream.

11. The process of claim 1, further comprising:
   (i) separating a first recycle stream comprising unreacted aliphatic monohydric alcohol from said crude product stream;
   (ii) recycling said first recycle stream to transesterification step (c);
   (iii) separating a second recycle stream comprising unreacted cyclic carbonate and said homogeneous carbonation catalyst from said crude product stream; and
   (iv) recycling at learnt a portion of said second recycle stream to said carbonation step (a) and/or at least a portion of said second recycle stream to said transesterification step (c).

12. The process of claim 2, wherein said cyclic carbonate is ethylene carbonate and said aliphatic monohydric alcohol is methanol.

13. The process of claim 1, wherein said second reaction zone is a reaction vessel selected from the group consisting of: a reactive distillation column, a distillation column with at least a plurality of reaction zones, a distillation column with a plurality of reaction zones having heat exchangers disposed between the distillation column and each reaction zone, and a distillation column with a plurality of reaction zones wherein bottoms thereof are optionally recycled to the distillation column.

14. An integrated process for the production of dialkyl carbonate and a diol from an alkylene oxide, carbon dioxide and an aliphatic monohydric alcohol consisting essentially of:
   (a) reacting an alkylene oxide with carbon dioxide in the presence of a homogeneous carbonation catalyst in a first reaction zone at a temperature in the range of about 50 to 250° C. and at a pressure of at least about 1379 kPa (200 psi) to provide a crude cyclic carbonate stream comprising a cyclic carbonate and homogeneous carbonation catalyst;
   (b) directing said crude cyclic carbonate stream into a second reaction zone; and
   (c) directing said cyclic carbonate with an aliphatic monohydric alcohol in said second reaction zone in the presence of said homogeneous carbonation catalyst to provide a crude product stream comprising a dialkyl carbonate and diol, wherein said crude cyclic carbonate stream has not been subjected to a separation other than to remove an amount of unreacted alkylene oxide, an amount of unreacted carbon dioxide, or both;
   wherein said homogeneous carbonation catalyst of (a) and (c) is a mixture comprising a halide containing component and a bicarbonate.

15. An integrated process for the production of dialkyl carbonate and a dial from an alkylene oxide, carbon dioxide and an aliphatic monohydric alcohol comprising:
   (a) reacting an alkylene oxide with carbon dioxide in the presence of a homogeneous carbonation catalyst in a first reaction zone at a temperature in the range of about 150 to 200° C. and its pressure of at least about 1379 kPa (200 psi) to provide a crude cyclic carbonate stream comprising a cyclic carbonate and homogeneous carbonation catalyst;
   (b) directing said crude cyclic carbonate stream into a second reaction zone; and
   (c) reacting said cyclic carbonate with an aliphatic monohydric alcohol in said second reaction zone in the presence of maid homogeneous carbonation catalyst at a temperature of about 75 to 170° C. to provide a crude product stream comprising a dialkyl carbonate and diol, wherein said crude cyclic carbonate stream has not been subjected to a separation other than to remove an amount of unreacted alkylene oxide, an amount of unreacted carbon dioxide, or both;
   (d) separating a first recycle stream comprising unreacted aliphatic monohydric alcohol from said crude product stream;
   (e) recycling said first recycle stream to transesterification step (c);
   (f) separating a second recycle stream comprising unreacted cyclic carbonate and said homogeneous carbonation catalyst from said crude product stream; and
   (g) recycling at least a portion of said second recycle stream to said carbonation step (a) and/or at least a portion of said second recycle stream to said transesterification step (c);
   wherein said homogeneous carbonation catalyst of (a), (c), and (f) is a mixture comprising a halide containing component and a bicarbonate.

16. The process of claim 1, wherein said bicarbonate comprises sodium bicarbonate and said halide containing component is selected from the group consisting of: potassium iodide, tetrabutyl ammonium bromide and mixtures thereof.

* * * * *